United States Patent
Zhang et al.

(10) Patent No.: US 9,004,752 B2
(45) Date of Patent: Apr. 14, 2015

(54) METHOD FOR EVALUATING THE SOLUBILITY OF A CRYSTALLINE SUBSTANCE IN A POLYMER

(75) Inventors: Geoff G. Zhang, Vernon Hills, IL (US); Lian Yu, Madison, WI (US); Jing Tao, Hillsborough, NJ (US); Ye Sun, Revere, MA (US); Markus Maegerlein, Mannheim (DE)

(73) Assignees: Abbvie, Inc., North Chicago, IL (US); Abbvie Deutschland GmbH & Co KG, Wiesbaden (DE); Wisconsin Alumni Research Foundation, Madison, WI (US)

( * ) Notice: Subject to any disclaimer, the term of this patent is extended or adjusted under 35 U.S.C. 154(b) by 727 days.

(21) Appl. No.: 12/989,396

(22) PCT Filed: Apr. 29, 2009

(86) PCT No.: PCT/EP2009/055233
§ 371 (c)(1),
(2), (4) Date: May 5, 2011

(87) PCT Pub. No.: WO2009/135799
PCT Pub. Date: Nov. 12, 2009

(65) Prior Publication Data
US 2011/0261857 A1 Oct. 27, 2011

Related U.S. Application Data

(60) Provisional application No. 61/050,413, filed on May 5, 2008.

(51) Int. Cl.
*G01N 25/14* (2006.01)
*G01K 17/06* (2006.01)
(Continued)

(52) U.S. Cl.
CPC ............ *G01N 33/15* (2013.01); *G01N 25/4866* (2013.01)

(58) Field of Classification Search
CPC . C08L 23/16; C08L 2666/04; C08L 2312/00; C08L 23/10

USPC .......... 374/4, 5, 29–36, 16, 43–45, 160, 159, 374/10–12; 422/51; 436/147; 702/130, 136
See application file for complete search history.

(56) References Cited

U.S. PATENT DOCUMENTS 4,908,801 A * 3/1990 Bell et al. ......................... 367/23
5,614,632 A * 3/1997 Bhupathy et al. ............. 546/180
(Continued)

FOREIGN PATENT DOCUMENTS

JP 2005111857 A * 4/2005

OTHER PUBLICATIONS

Form PCT/ISA/201 WO, Nov. 12, 2009, ISR for PCT EP/2009/055233.
(Continued)

*Primary Examiner* — Gail Kaplan Verbitsky
(74) *Attorney, Agent, or Firm* — Saul Ewing LLP; Peter C. Lauro, Esq.

(57) ABSTRACT

A viable strategy to enhance the bioavailability of poorly soluble drugs is to use amorphous solids in place of the more commonly used crystalline solids in pharmaceutical formulations. However, amorphous solids are physically metastable and tend to revert back to their crystalline counterpart. An effective approach to stabilizing an amorphous drug against crystallization is to disperse it in a polymer matrix. The drug's solubility in the chosen polymer defines the upper limit of drug loading without any risk of crystallization. Measuring the solubility of a drug in a polymer has been a scientific and technological challenge because the high viscosity of polymers makes achieving solubility equilibrium difficult and because pharmaceutically important drug/polymer dispersions are glasses, which undergo structural relaxation over time. The invention provides a method based on Differential Scanning calorimetry (DSC) for measuring the solubility of crystalline drugs in polymeric matrices. The method relies on the detection of the dissolution endpoint of a drug/polymer mixture prepared by cryomilling.

8 Claims, 9 Drawing Sheets

Where curves 1 and 3 are $T_{end}$-composition curves, curves 2 and 4 are $T_g$-composition curves, UCLs of a–d are obtained by intersecting the following pairs of curves 1–4:
a: Curves 1 and 2;   b: Curves 1 and 4;
c: Curves 3 and 2;   d: Curves 3 and 4;

(51) Int. Cl.
*G01N 33/15* (2006.01)
*G01N 25/48* (2006.01)

(56) References Cited

U.S. PATENT DOCUMENTS

| | | | | |
|---|---|---|---|---|
| 5,652,365 | A | * | 7/1997 | McCauley et al. ............... 546/77 |
| RE36,736 | E | * | 6/2000 | Davis et al. .................... 548/466 |
| 6,469,179 | B1 | * | 10/2002 | Albano et al. ................. 548/455 |
| 6,486,338 | B1 | * | 11/2002 | Hanelt et al. .................. 556/438 |
| 6,543,931 | B2 | * | 4/2003 | Sauvant et al. ................. 374/21 |
| 8,142,765 | B2 | * | 3/2012 | Ferrari ............................ 424/63 |
| 8,518,738 | B2 | * | 8/2013 | Sirringhaus et al. ............ 438/99 |
| 2005/0261466 | A1 | * | 11/2005 | Shalaby ........................ 528/354 |
| 2007/0087132 | A1 | * | 4/2007 | Greener et al. ................ 428/1.1 |
| 2008/0049173 | A1 | * | 2/2008 | Matsufuji et al. ............... 349/96 |
| 2009/0169737 | A1 | * | 7/2009 | Bremer ......................... 427/222 |
| 2009/0180059 | A1 | * | 7/2009 | Fukuda et al. .................. 349/96 |
| 2009/0274759 | A1 | * | 11/2009 | Bar-Shalom et al. ......... 424/484 |
| 2011/0065866 | A1 | * | 3/2011 | Leibler et al. ................. 525/186 |
| 2011/0097575 | A1 | * | 4/2011 | Pratte et al. ................... 428/336 |
| 2011/0256406 | A1 | * | 10/2011 | Farrell et al. .................. 428/412 |
| 2014/0012534 | A1 | * | 1/2014 | Prest et al. .................... 702/136 |

OTHER PUBLICATIONS

Form PCT/ISA/201 WO, Nov. 12, 2009, Written Opinion for PCT/EP2009/055233.

Tamagawa R.E. et al: "Short-cut method to predict the solubility of organic molecules in aqueous and nonaqueous solutions by Differential Scanning Calorimetry". Crystal Growth & Design, vol. 6, No. 1, Sep. 9, 2005 pp. 313-320.

Rajeev Mohan, Heike Lorenz, Allan S. Myerson: "Solubility Measurement Using Differential Scanning Calorimetry" Industrial and Engineering Chemistry Research, vol. 41, Jul. 8, 2002, pp. 4854-4862.

M. Vasanthavada: Wei-Qin Tong; Y. Joshi; M.S. Kislalioglu; "Phase Behaviour of Amorphous Molecular Dispersions II: Role of Hydrogen Bonding in Solid Solubility and Phase Separation Kinetics", Pharmaceutical Research, vol. 22, No. 3, Mar. 1, 2005, pp. 440-448.

Vasanthavada, M.; Tong, W.; Joshi, Y.; Kislalioglu, M. S. Pharm. Res. 2004, 21, 1598-1606.

Vasanthavada, M.; Tong, W.; Joshi, Y.; Kislalioglu, M. S. Pharm. Res. 2005, 22, 440-448.

Marsac, P. J.; Shamblin, S. L.; Taylor, L. S. Pharm. Res. 2006, 23, 2417-2426.

Mohan, R.; Lorenz, H.; Myerson, A. Ind. Eng. Chem. Res. 2002, 41, 4854-4862.

Park, K.; Evans, J. M. B.; Myerson, A Cryst. Growth & Des. 2003, 3, 991-995.

Tamagawa, R.; Martins, W.; Derenzo, S.; Bernardo, A.; Rolemberg, M.; Carvan, P.; Giulietti, M. Cryst. Growth & Des. 2006, 6(1), 313-320.

* cited by examiner

Where curves 1 and 3 are $T_{end}$-composition curves, curves 2 and 4 are $T_g$-composition curves, UCLs of a–d are obtained by intersecting the following pairs of curves 1–4:
    a: Curves 1 and 2;        b: Curves 1 and 4;
    c: Curves 3 and 2;        d: Curves 3 and 4;

METHOD FOR EVALUATING THE SOLUBILITY OF A CRYSTALLINE SUBSTANCE IN A POLYMER

This application is the U.S. national phase, pursuant to 35 U.S.C. §371, of PCT international application Ser. No. PCT/EP2009/055233, filed Apr. 29, 2009, designating the United States and published in English on Nov. 12, 2009 as publication WO 2009/135799 A2, which claims priority to U.S. Provisional Patent Application Ser. No. 61/050,413, filed May 5, 2008. The entire contents of the aforementioned patent applications are incorporated herein by this reference.

Pharmaceutical scientists increasingly face the challenge of delivering poorly water soluble drugs. To meet this challenge, attempts have been made to use amorphous solids in place of crystals in pharmaceutical formulations. Amorphous solids are preferred physical forms because they dissolve more rapidly than crystalline solids when contacted with a liquid medium such as gastric fluid. The ease of dissolution may be attributed at least in part to the fact that the energy required for dissolution of an amorphous drug is less than that required for the dissolution of a crystalline or microcrystalline solid phase.

To make this approach a practical reality in drug development, however, new engineering techniques must be developed to stabilize amorphous drugs and counteract their tendency to undergo physical and chemical changes. One way of stabilizing the amorphous state of a drug involves forming solid solutions of the drug in polymeric matrices.

Drug solubility in polymeric matrices is an important physical property that affects the stability of drugs in amorphous formulations. This property is important for selecting appropriate polymers and designing formulations for the delivery of amorphous drugs. For example, it defines the upper limit of drug loading without risk of crystallization. Despite its importance, there has been no standard technique for measuring the solubility of a drug in a polymer. The difficulty largely arises from the high viscosity of polymers, which makes achieving solubility equilibrium difficult.

Vasanthavada et al. used moisture to induce the crystallization of trehalose from an amorphous mixture with dextran or PVP, and compared the eventual glass transition temperature Tg of the system with the Tgs of the amorphous mixtures of trehalose and polymer to calculate trehalose's solubility in the polymer (Vasanthavada, M.; Tong, W.; Joshi, Y.; Kislalioglu, M. S. Pharm. Res. 2004, 21, 1598-1606; Vasanthavada, M.; Tong, W.; Joshi, Y.; Kislalioglu, M. S. Pharm. Res. 2004, 22, 440-448). The method is subject to errors because of the effect of water on the solubility of drug in the polymer, and the effect of residual water on the Tg measurement.

Marsac et al. developed a predictive model of drug-polymer solubility based on the Flory-Huggins theory of liquids (Marsac, P. J.; Shamblin, S. L.; Taylor, L. S. Pharm. Res. 2006, 23, 2417-2426). The model has been calibrated on the solubility in a monomer solvent, but has never been tested with experimentally measured solubility in polymers.

Another difficulty encountered in studying drug/polymer solubility is the fact that pharmaceutically important drug/polymer dispersions are glasses, which are kinetically frozen liquids. Despite their low molecular mobility, glasses are characterized by their slow relaxation over time toward the equilibrium liquid state (the state that the system would reach if it were not kinetically frozen). This means that the solubility for a glassy drug/polymer system is not unique, and depends on the age of the mixture. The model of Marsac et al., and models based on equilibrium thermodynamics in general, predict solubility for fully relaxed, equilibrium liquids. In practice, however, structural relaxation of a glass is so slow that reaching the equilibrium liquid state may take years or even decades. For the shelf stability of pharmaceuticals, what is relevant is the solubility in the metastable glass, not the solubility in the equilibrium liquid.

A major aim of this invention is to measure drug/polymer solubility near the glass transition temperature. Due to the low molecular mobility of glasses, measuring solubility in a glassy state is impractically slow. We employed DSC, a convenient technique available in most laboratories, to measure the solubility of small-molecule crystals in polymers.

DSC has been used to measure the solubility of small-molecule crystals in small-molecule solvents (Mohan, R.; Lorenz, H.; Myerson, A. Ind. Eng. Chem. Res. 2002, 41, 4854-4862; Park, K.; Evans, J. M. B.; Myerson, A. Cryst. Growth & Des. 2003, 3, 991-995, Tamagawa, R.; Martins, W.; Derenzo, S.; Bernardo, A.; Rolemberg, M.; Carvan, P.; Giulietti, M. Cryst. Growth & Des. 2006, 6(1), 313-320). The method involves heating a crystal/solvent slurry of known composition x to slowly dissolve the crystals in the solvent and detecting the final temperature of crystal dissolution, $T_{end}$. If phase equilibrium is maintained during heating, the solubility of the crystal in the solvent is x at $T_{end}$.

The invention seeks to provide a method for evaluating the solubility of a crystalline substance, in particular a pharmaceutically active ingredient, in a polymer at different temperatures, which can be used to predict the storage stability of a dosage form containing a solid solution of a pharmaceutically active ingredient in a polymer.

This invention provides a method for evaluating the solubility of a crystalline substance in a polymer, comprising
a) providing an intimate mixture of the crystalline substance and the polymer,
b) heating the intimate mixture while recording the DSC dissolution endotherm of the mixture,
c) determining an endset temperature of dissolution $T_{end}$ from the DSC dissolution endotherm,
d) taking $T_{end}$ as the temperature at which the crystalline substance dissolves completely in the polymer.

The invention further provides a method for evaluating the solubility of a crystalline substance in a polymer as a function of temperature, comprising
a) providing a plurality of intimate mixtures of crystalline substance and polymer with different compositions,
b) determining $T_{end}$ of each of the intimate mixtures,
c) plotting $T_{end}$ over the composition of the mixtures.

The invention further provides a method for evaluating the solubility of a crystalline substance in a polymer at the glass transition temperature Tg, comprising
a) establishing the solubility of the crystalline substance in the polymer as a function of temperature,
b) providing a plurality of crystalline substance/polymer mixtures with different compositions and determining Tg of a liquid formed by melting each of the mixtures,
c) plotting Tg over the composition of the mixtures,
d) determining the solubility at Tg as the intersection of the $T_{end}$ plot and the Tg plot.

The invention further provides a method for predicting the storage stability of a dosage form which contains a solid solution of a pharmaceutically active ingredient in a polymer, the method comprising
a) determining an upper concentration limit as the solubility of the pharmaceutically active ingredient in the polymer at the glass transition temperature Tg,
b) comparing the proportion of the pharmaceutically active ingredient in the solid solution with the upper concentration limit.

c) assigning a solid solution whose drug loading is below the upper concentration limit as likely stable against crystallization If the drug loading of the solid solution is below the upper concentration limit, the dosage form is stable against crystallization; if the drug loading of the solid dispersion is above the upper concentration limit, the dosage form should be kept at temperatures well below the Tg of the solid solution.

In addition to examining physical stability of amorphous solid solutions and identifying the safe storage conditions for such formulations, the upper concentration limit (UCL) estimated for pairs of crystalline substances and polymers can be further utilized in the designing and optimizing formulations of amorphous solid solutions, also from the physical stability viewpoint. Different polymers could be used for formulation development. Various auxiliary components, such as surfactants, could be added to the formulation as well.

The term "composition" of a crystalline substance/polymer mixture as used herein refers to the weight of the crystalline substance, relative to the combined weight of the crystalline substance and the polymer, expressed as a percentage. Suitably, the composition may be within the range from 1% to 99% w/w of the crystalline substance, for example 5% to 95%.

In the invention, a DSC method is used to record the dissolution endotherm of a crystalline substance/polymer mixture. Differential scanning calorimetry, or DSC, is a thermoanalytical technique in which the difference in the amount of heat required to increase the temperature of a sample and a reference are measured as a function of temperature. Both the sample and the reference are maintained at nearly the same temperature throughout the experiment. Generally, the temperature program for a DSC analysis is designed such that the sample holder temperature increases linearly as a function of time. The reference sample has a well-defined heat capacity over the range of temperatures to be scanned. The basic principle underlying this technique is that, when the sample undergoes a physical transformation such as phase transitions, more (or less) heat will need to flow to it than to the reference to maintain both at the same temperature. Whether more or less heat is needed flow to the sample depends on whether the process is exothermic or endothermic.

As the crystalline substance dissolves in the polymer, the sample generally undergoes an endothermic phase transition. In the DSC endotherm, a corresponding transition peak will be observed. The temperature where the peak transition returns to the baseline is known as the endset temperature $T_{end}$. The endset temperature may be constructed by the intersection of the greatest slope tangent of the tailing edge of the peak with the extrapolated baseline of the DSC curve.

Because dissolution of the drug in the polymer matrix requires the transport of materials, how well the components are mixed affects how well the endpoint of dissolution is detected by DSC. If the components are poorly mixed and contain large particles, dissolution requires material transport over long distances. When this mixture is analyzed by DSC at a fixed heating rate, the endpoint of dissolution will be higher. Accordingly, the mixture of the crystalline substance and the polymer should be as intimate as possible without, however, completely losing crystallinity.

Various milling or grinding techniques known in the art may be employed, such as hand milling, ball milling and the like. The frictional heat generated in conventional dry grinding may be detrimental to retaining crystallinity. Therefore, controlling the temperature during milling is preferable. We found that cryomilling (also referred to as cryogenic milling, cryogenic grinding or freezer milling) the drug/polymer mixture before DSC is an effective way to improve mixing and help achieve solubility equilibrium. Cryomilling is a variation of mechanical milling, in which a powder is milled in a cryogen (usually liquid nitrogen) slurry or at a cryogenic temperature.

In preferred embodiments, the intimate mixture is obtained by joint cryomilling of the crystalline substance and the polymer. Suitable cryomilling times range from 1 min to 60 min. An optimal time of cryomilling can be determined by increasing the milling time until the point of diminishing return. The crystalline substance and the polymer may also be milled separately, combined, and further cryomilled together.

To ensure that phase equilibrium is maintained, slow heating rates are preferred. Heating rates in the range from 2.5° C./min to 0.05° C./min, mostly 2.0° C./min to 0.1° C./min, are generally suitable. In a preferred embodiment, the DSC dissolution endotherm is recorded at a plurality of heating rates and $T_{end}$ is extrapolated to zero heating rate.

For the purposes of the present invention, the crystalline substance/polymer solubility near the glass transition temperature is of particular interest. The glass transition temperature Tg of the pure polymer is generally known. Dissolved substances in the polymer, however, could exert a plasticizing effect on the polymer and thus depress the Tg of the polymer such that the crystalline substance/polymer solid solution has a somewhat lower Tg than the starting polymer used for its preparation. Accordingly, the Tg depends on the composition of the mixture. The Tg—composition relation can be established by determining the Tg associated with homogeneous amorphous substance/polymer mixtures having different compositions, and plotting Tg over the composition of the mixtures.

The Tg associated with a homogeneous amorphous drug/polymer mixture is conveniently determined by a DSC method, in particular by modulated DSC. The glass transition is observed as a step-like change in the DSC curve, which results from the increase of heat capacity when a solid glass is heated to become a viscous liquid.

The crystalline substance may be any chemical substance of interest that is present in its crystalline state. In preferred embodiments, however, the crystalline substance is a pharmaceutically active ingredient (drug). Pharmaceutically active ingredients are biologically active agents and include those which exert a local physiological effect, as well as those which exert a systemic effect, after oral administration. The invention is particularly useful for water-insoluble or poorly water-soluble (or "hydrophobic" or "lipophilic") compounds. Compounds are considered water-insoluble or poorly water-soluble when their solubility in water at 25° C. is less than 1 g/100 ml, especially less than 0.1 g/100 ml.

Examples of suitable pharmaceutically active ingredients include, but are not limited to:

analgesic and anti-inflammatory drugs such as fentanyl, indomethacin, ibuprofen, naproxene, diclofenac, diclofenac sodium, fenoprofen, acetylsalicylic acid, ketoprofen, nabumetone, paracetamol, piroxicam, meloxicam, tramadol, and COX-2 inhibitors such as celecoxib and rofecoxib;

anti-arrhythmic drugs such as procainamide, quinidine and verapamil;

antibacterial and antiprotozoal agents such as amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, nortloxacin, ofloxacin, oxacillin, phenoxymethyl-penicillin potassium, pyrimethaminesulfadoxime and streptomycin;

anti-coagulants such as warfarin;

antidepressants such as amitriptyline, amoxapine, butriptyline, clomipramine, desipramine, dothiepin, doxepin, fluoxetine, reboxetine, amineptine, selegiline, gepirone, imipramine, lithium carbonate, mianserin, milnacipran, nortriptyline, paroxetine, sertraline and 3-[2-[3,4-dihydrobenzofuro[3,2-c]pyridin-2(1H)-yl]ethyl]-2-methyl-4H-pyrido[1,2-a]pyrimidin-4-one;

anti-diabetic drugs such as glibenclamide and metformin;

anti-epileptic drugs such as carbamazepine, clonazepam, ethosuximide, gabapentin, lamotrigine, levetiracetam, phenobarbitone, phenyloin, primidone, tiagabine, topiramate, valpromide and vigabatrin;

antifungal agents such as amphotericin, clotrimazole, econazole, fluconazole, flucytosine, griseofulvin, itraconazole, ketoconazole, miconazole nitrate, nystatin, terbinafine and voriconazole;

antihistamines such as astemizole, cinnarizine, cyproheptadine, decarboethoxyloratadine, fexofenadine, flunarizine, levocabastine, loratadine, norastemizole, oxatomide, promethazine and terfenadine;

anti-hypertensive drugs such as captopril, enalapril, ketanserin, lisinopril, minoxidil, prazosin, ramipril, reserpine, terazosin and telmisartan;

anti-muscarinic agents such as atropine sulphate and hyoscine;

antineoplastic agents and antimetabolites such as platinum compounds, such as cisplatin and carboplatin; taxanes such as paclitaxel and docetaxel; tecans such as camptothecin, irinotecan and topotecan; vinca alkaloids such as vinblastine, vindecine, vincristine and vinorelbine; nucleoside derivatives and folic acid antagonists such as 5-fluorouracil, capecitabine, gemcitabine, mercaptopurine, thioguanine, cladribine and methotrexate; alkylating agents such as the nitrogen mustards, e.g. cyclophosphamide, chlorambucil, chiormethine, iphosphamide, melphalan, or the nitrosoureas, e.g. carmustine, lomustine, or other alkylating agents, e.g. busulphan, dacarbazine, procarbazine, thiotepa; antibiotics such as daunorubicin, doxorubicin, idarubicin, epirubicin, bleomycin, dactinomycin and mitomycin; HER 2 antibodies such as trastuzumab; podophyllotoxin derivatives such as etoposide and teniposide; farnesyl transferase inhibitors; anthrachinon derivatives such as mitoxantron;

anti-migraine drugs such as alniditan, naratriptan and sumatriptan;

anti-Parkinsonian drugs such as bromocryptine mesylate, levodopa and selegiline;

antipsychotic, hypnotic and sedating agents such as alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone and zolpidem;

anti-stroke agents such as lubeluzole, lubeluzole oxide, riluzole, aptiganel, eliprodil and remacemide;

antitussives such as dextromethorphan and laevodropropizine;

antivirals such as acyclovir, ganciclovir, loviride, tivirapine, zidovudine, lamivudine, zidovudine/lamivudine, didanosine, zalcitabine, stavudine, abacavir, lopinavir, amprenavir, nevirapine, efavirenz, delavirdine, indinavir, nelfinavir, ritonavir, saquinavir, adefovir and hydroxyurea;

beta-adrenoceptor blocking agents such as atenolol, carvedilol, metoprolol, nebivolol and propanolol;

cardiac inotropic agents such as aminone, digitoxin, digoxin and milrinone;

corticosteroids such as beclomethasone dipropionate, betamethasone, budesonide, dexamethasone, hydrocortisone, methylprednisolone, prednisolone, prednisone and triamcinolone;

disinfectants such as chlorhexidine; diuretics such as acetazolamide, furosemide, hydrochlorothiazide and isosorbide;

enzymes;

gastro-intestinal agents such as cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel and sulphasalazine;

haemostatics such as aminocaproic acid;

HIV protease inhibiting compounds such as ritonavir, lopinavir, indinavir, saquinavir, 5(S)-Boc-amino-4(S)-hydroxy-6-phenyl-2(R)phenylmethylhexanoyl-(L)-Val-(L)-Phemorpholin-4-ylamide, 1-Naphthoxyacetyl-beta-methylthio-Ala-(2S,3S)3-amino-2-hydroxy-4-butanoyl 1,3-thiazolidine-4-t-butylamide, 5-isoquinolinoxyacetyl-betamethylthio-Ala-(2S,3S)-3-amino-2-hydroxy-4-butanoyl-1,3-thiazolidine-4-t-butylamide, [1S-[1R-(R-),2S*])-N'[3-[[[(1,1-dimethylethyl)amino]carbonyl](2-methylpropyl)amino]-2hydroxy-1-(phenylmethyl)propyl]-2-[(2-quinolinylcarbonyl)amino]-butanediamide, amprenavir; DMP-323; DMP-450; nelfinavir, atazanavir, tipranavir, palinavir, darunavir, RO033-4649, fosamprenavir, P-1946, BMS 186,318, SC-55389a; BILA 1906 BS, tipranavir;

lipid regulating agents such as atorvastatin, fenofibrate, fenofibric acid, lovastatin, pravastatin, probucol and simvastatin;

local anaesthetics such as benzocaine and lignocaine;

opioid analgesics such as buprenorphine, codeine, dextromoramide, dihydrocodeine, hydrocodone, oxycodone and morphine;

parasympathomimetics and anti-dementia drugs such as AIT-082, eptastigmine, galanthamine, metrifonate, milameline, neostigmine, physostigmine, tacrine, donepezil, rivastigmine, sabcomeline, talsaclidine, xanomeline, memantine and lazabemide;

peptides and proteins such as antibodies, becaplermin, cyclosporine, tacrolimus, erythropoietin, immunoglobulins and insulin;

sex hormones such as oestrogens: conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxyprogesterone acetate, megestrol, norethindrone, norethindrone acetate, norethisterone, norethisterone acetate, norethynodrel, norgestimate, norgestrel, norgestrienone, progesterone and quingestanol acetate;

stimulating agents such as sildenafil, vardenafil;

vasodilators such as amlodipine, buflomedil, amyl nitrite, diltiazem, dipyridamole, glyceryl trinitrate, isosorbide dinitrate, lidoflazine, molsidomine, nicardipine, nifedipine, oxpentifylline and pentaerythritol tetranitrate;

their N-oxides, their pharmaceutically acceptable acid or base addition salts and their stereochemically isomeric forms.

Pharmaceutically acceptable acid addition salts comprise the acid addition salt forms which can be conveniently obtained by treating the base form of the active ingredient with appropriate organic and inorganic acids.

Active ingredients containing an acidic proton may be converted into their non-toxic metal or amine addition salt forms by treatment with appropriate organic and inorganic bases.

The term "addition salt" also comprises the hydrates and solvent addition forms which the active ingredients are able to form. Examples of such forms are hydrates, alcoholates and the like.

The N-oxide forms of the active ingredients comprise those active ingredients in which one or several nitrogen atoms are oxidized to the so-called N-oxide.

The term "stereochemically isomeric forms" defines all possible stereoisomeric forms which the active ingredients may possess. In particular, stereogenic centers may have the R- or S-configuration and active ingredients containing one or more double bonds may have the E- or Z-configuration.

The polymer may be any polymeric matter of interest. For the envisaged use of the solid solution as a dosage form for the delivery of a pharmaceutically active ingredient to a subject, in particular a human, the polymer is, however, preferably a pharmaceutically acceptable polymer.

The pharmaceutically acceptable polymer may be selected from water-soluble polymers, water-dispersible polymers or water-swellable polymers or any mixture thereof. Polymers are considered water-soluble if they form a clear homogeneous solution in water. When dissolved at 20° C. in an aqueous solution at 2% (w/v), the water-soluble polymer preferably has an apparent viscosity of 1 to 5000 mPa·s, more preferably of 1 to 700 mPa·s, and most preferably of 5 to 100 mPa·s. Water-dispersible polymers are those that, when contacted with water, form colloidal dispersions rather than a clear solution. Upon contact with water or aqueous solutions, water-swellable polymers typically form a rubbery gel.

Preferably, the pharmaceutically acceptable polymer has a Tg of at least 40° C., preferably at least 50° C., most preferably from 80° to 180. ° C. "Tg" means glass transition temperature. Methods for determining the Tg values of organic polymers are described in "Introduction to Physical Polymer Science", 2nd Edition by L. H. Sperling, published by John Wiley & Sons, Inc., 1992. The Tg value can be calculated as the weighted sum of the Tg values for homopolymers derived from each of the individual monomers, i, that make up the polymer: $Tg = \Sigma W_i X_i$, where W is the weight percent of monomer i in the organic polymer, and X is the Tg value for the homopolymer derived from monomer i. The Tg values for the homopolymers may be taken from "Polymer Handbook", 2nd Edition by J. Brandrup and E. H. Immergut, Editors, published by John Wiley & Sons, Inc., 1975.

For example, preferred pharmaceutically acceptable polymers can be selected from
homopolymers of N-vinyl lactams, especially polyvinylpyrrolidone (PVP); different grades of commercially available PVP are PVP K-12, PVP K-15, PVP K-17, PVP K-20, PVP K-30, PVP K-60, PVP K-90 and PVP K-120. The K-value referred to in this nomenclature is calculated by Fikentscher's formula from the viscosity of the PVP in aqueous solution, relative to that of water;
copolymers of N-vinyl lactams, especially copolymers of N-vinyl pyrrolidone and vinyl acetate or copolymers of N-vinyl pyrrolidone and vinyl propionate, cellulose esters and cellulose ethers, in particular methylcellulose and ethylcellulose, hydroxyalkylcelluloses, in particular hydroxypropylcellulose, hydroxyalkylalkylcelluloses, in particular hydroxypropylmethylcellulose, cellulose phthalates or succinates, in particular cellulose acetate phthalate and hydroxypropylmethylcellulose phthalate, hydroxypropylmethylcellulose succinate or hydroxypropylmethylcellulose acetate succinate;
high molecular polyalkylene oxides such as polyethylene oxide and polypropylene oxide and copolymers of ethylene oxide and propylene oxide,
polyvinyl alcohol-polyethylene glycol-graft copolymers (available as Kollicoat® IR from BASF AG, Ludwigshafen, Germany);
polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates),
polyacrylamides,
vinyl acetate polymers such as copolymers of vinyl acetate and crotonic acid, partially hydrolyzed polyvinyl acetate (also referred to as partially saponified "polyvinyl alcohol"), polyvinyl alcohol,
oligo- and polysaccharides such as carrageenans, galactomannans and xanthan gum, or mixtures of one or more thereof.

Among these, homopolymers or copolymers of N-vinyl pyrrolidone, in particular a copolymer of N-vinyl pyrrolidone and vinyl acetate, are preferred. A particularly preferred polymer is a copolymer of 60% by weight of the copolymer, N-vinyl pyrrolidone and 40% by weight of the copolymer, vinyl acetate.

The invention is illustrated by the appended drawings and the examples which follow.

Figure 8A:
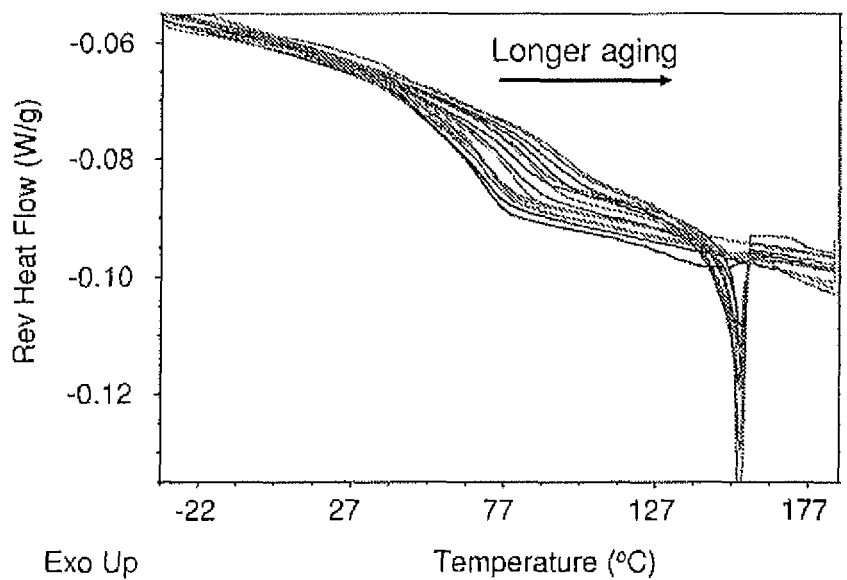
Figure 8B:
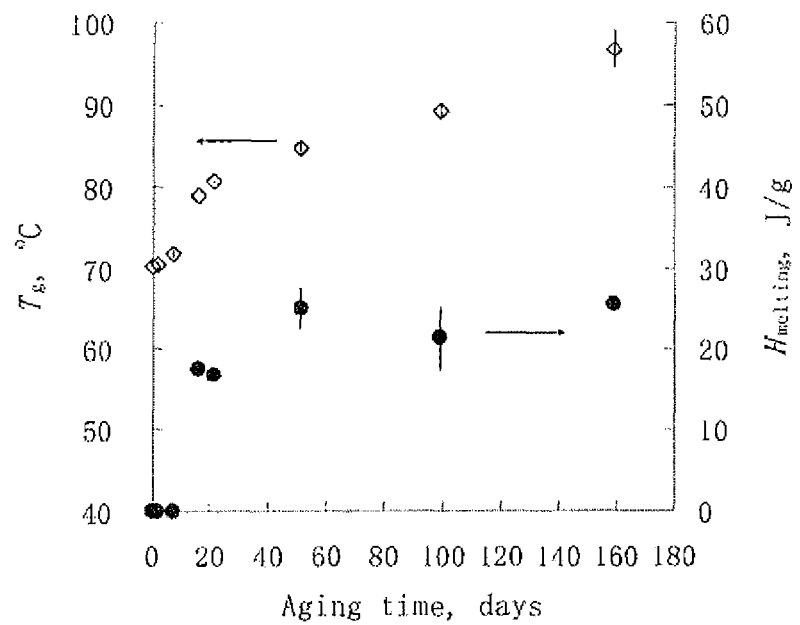

FIG. 8A (top) and FIG. 8B (bottom) show DSC traces and data plots showing the increase of $T_g$ and area of D-mannitol melting endotherm of a 30% D-mannitol/PVP mixture with aging time at 105° C.

Figure 9:
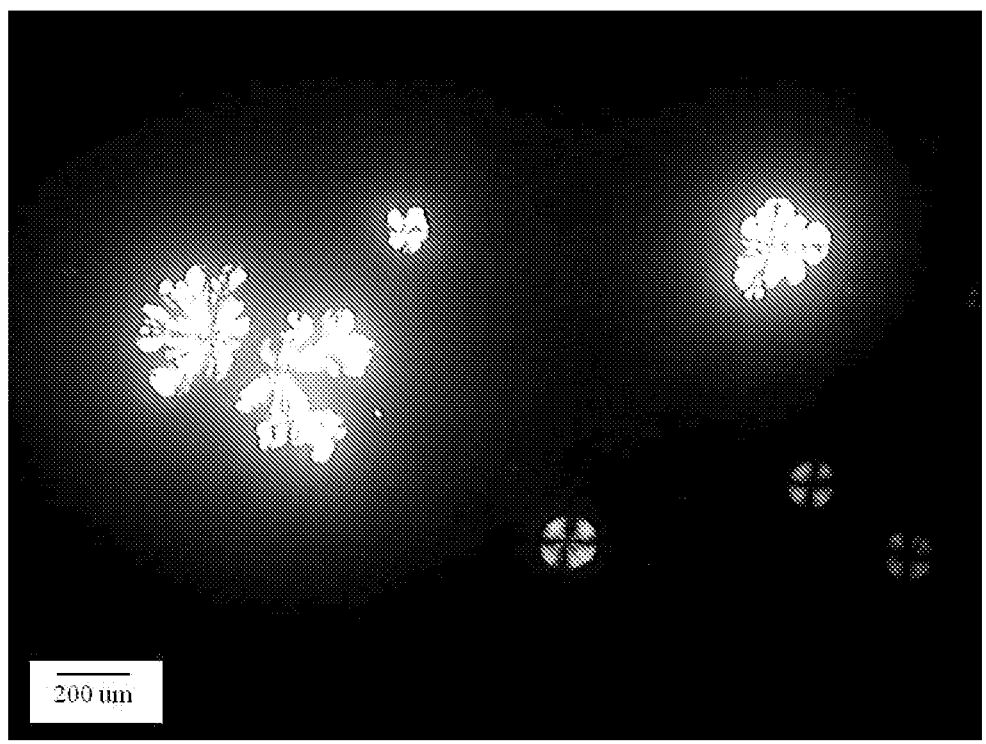

FIG. 9 shows crystals of D-mannitol formed during aging in method II.

Figure 10:
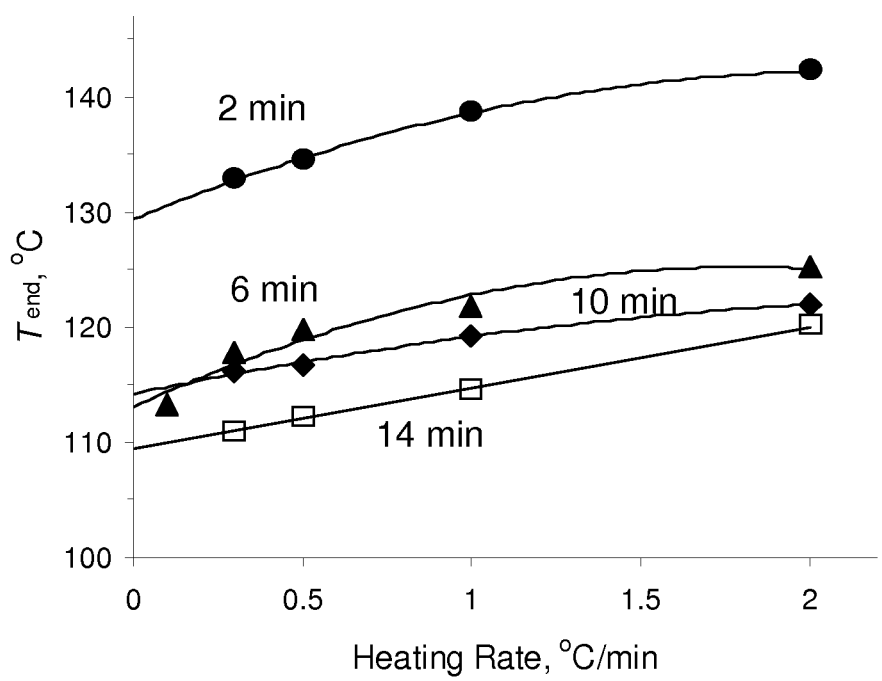

FIG. 10 shows the solubility temperature of 40% w/w IMC in PVPVA64 as a function of heating rates after cryomilling for different times.

Figure 11:
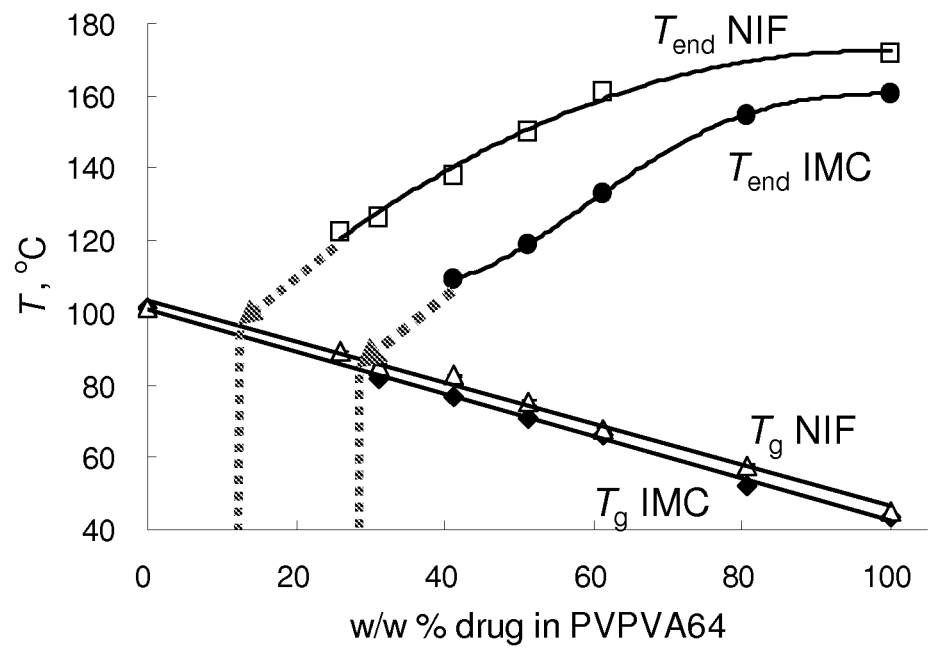

FIG. 11 shows dissolution endpoints $T_{end}$ and glass transition temperatures Tg of IMC/PVPVA and NIF/PVPVA as a function of solute concentration.

Figure 12:
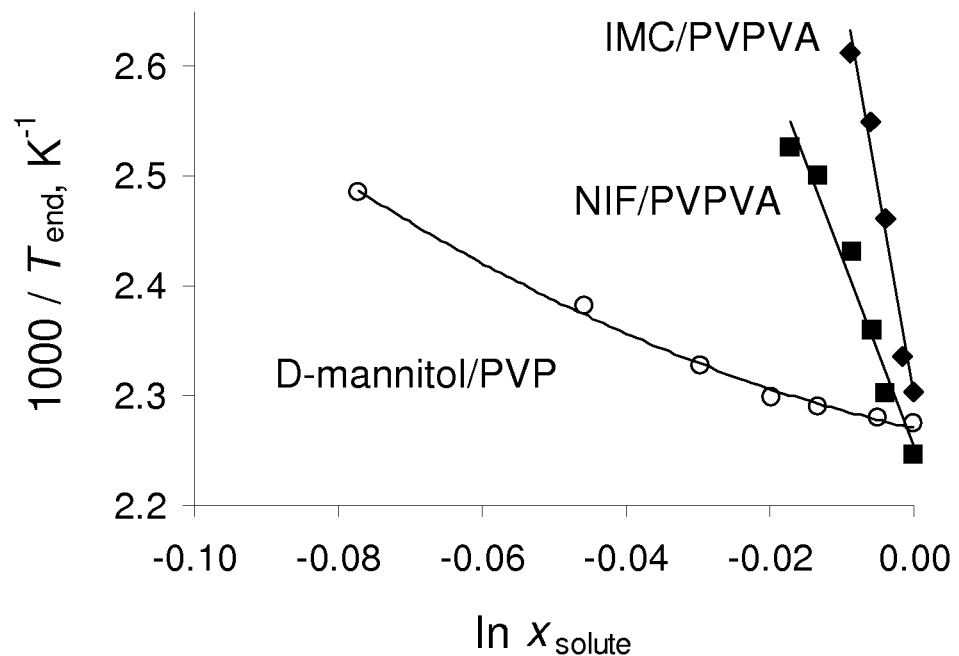

FIG. 12 shows solubility—temperature relations for the three systems studied.

Figure 13:
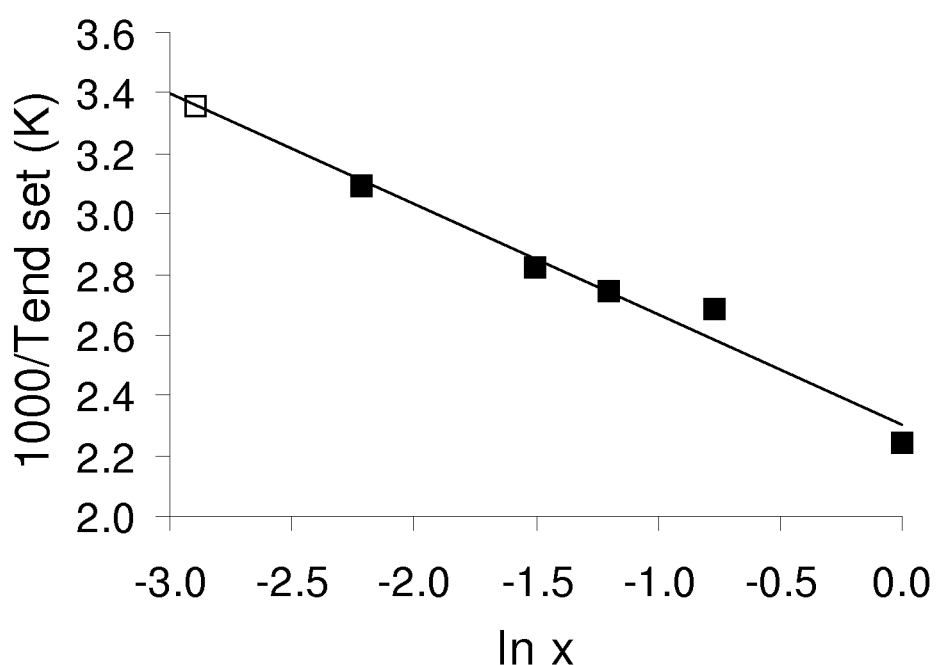

FIG. 13 shows that solubility of NIF in NMP measured by Method I (solid symbol) agree with that reported at 25° C. (empty symbol).

Figure 14:
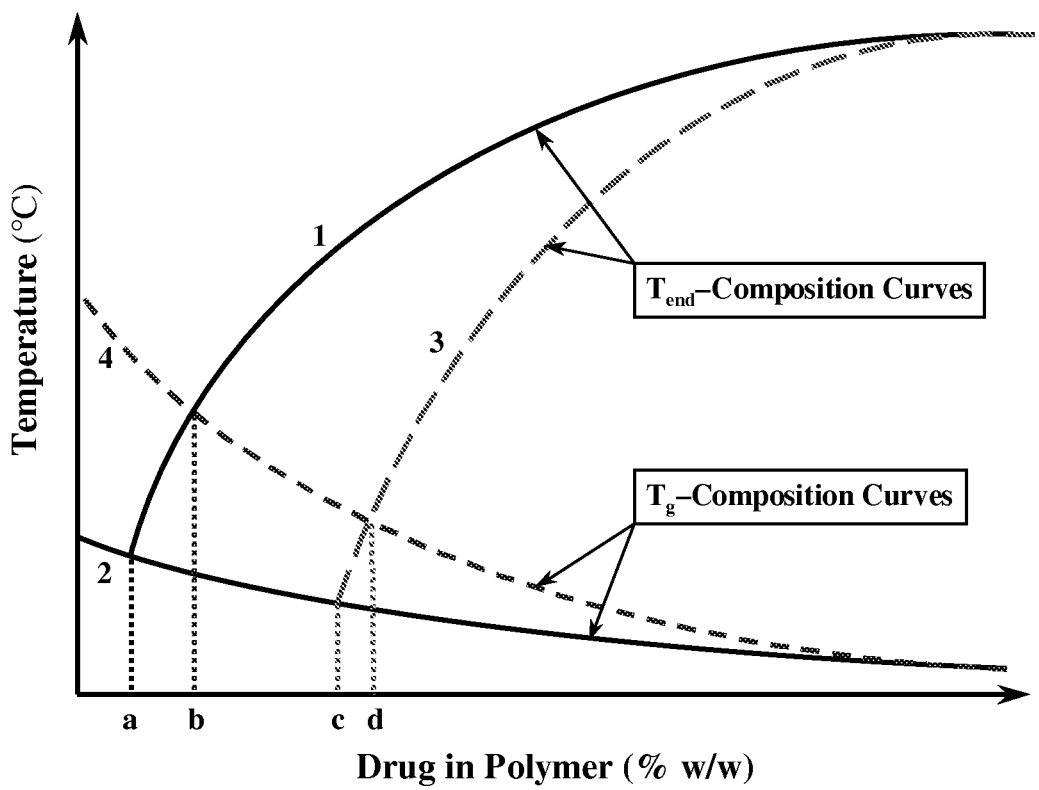

FIG. 14 shows several theoretical approaches to increase the upper concentration limit UCL of a solid solution.

EXAMPLES

D-mannitol (99+%, polymorph β), Nifedipine (NIF, in the α polymorph), a calcium channel blocker, and indomethacin (IMC, in the γ polymorph), a nonsteroidal anti-inflammatory agent, were obtained from Sigma-Aldrich. Polyvinyl pyrrolidone (PVP, K=15) was obtained from GAF Chemicals. PVPVA (Kollidone VA64, MW=45000-70000) was obtained from BASF. It was a 60:40 vinyl pyrrolidone-vinyl acetate copolymer (Tg=101° C.). It is less hygroscopic than PVP K15.

A cryogenic impact mill (SPEX CertiPrep model 6750) was used to prepare different concentrations of solute-polymer mixtures. In a typical procedure, 0.5-1 g of solute/polymer powder was milled at 10 Hz. Each cycle of milling was 2 min, followed by a 2 min cool-down. The cycle was repeated to achieve a desired milling time (16-60 min).

Standard and modulated differential scanning calorimetry (DSC) was conducted in hermetic aluminium pans using a TA Instruments DSC Q1000. 5-10 mg of the sample was packed into the pans. A pin hole was made in the lid to allow the escape of moisture. Standard DSC was performed at heating rates from 0.1 to 3° C./min. Modulated DSC was used to observe the glass transition of the amorphous phase at a heating rate of 2° C./min with the temperature modulating at ±0.5° C. every 60 second.

To set up an aging experiment, the sample was added into an open DSC pan and heated up on a microscope hot-stage (Linkam THMS 600) to Tm+20° C. under vacuum. The application of vacuum removed air bubbles trapped in the viscous melt. The pan was then quenched to room temperature, sealed immediately, and aged in an oven of known temperature.

X-ray diffraction was performed with a Bruker D8 Advance diffractometer (Cu Kα radiation, voltage 40 kV, and current 40 mA). The sample was ground with mortar and pestle, placed on a zero-background silicon (510) sample holder, and scanned from 2° to 50° at a speed of 1°/min and a step size of 0.02°.

Example 1

Influence of the Mixing Method

Figure 1:
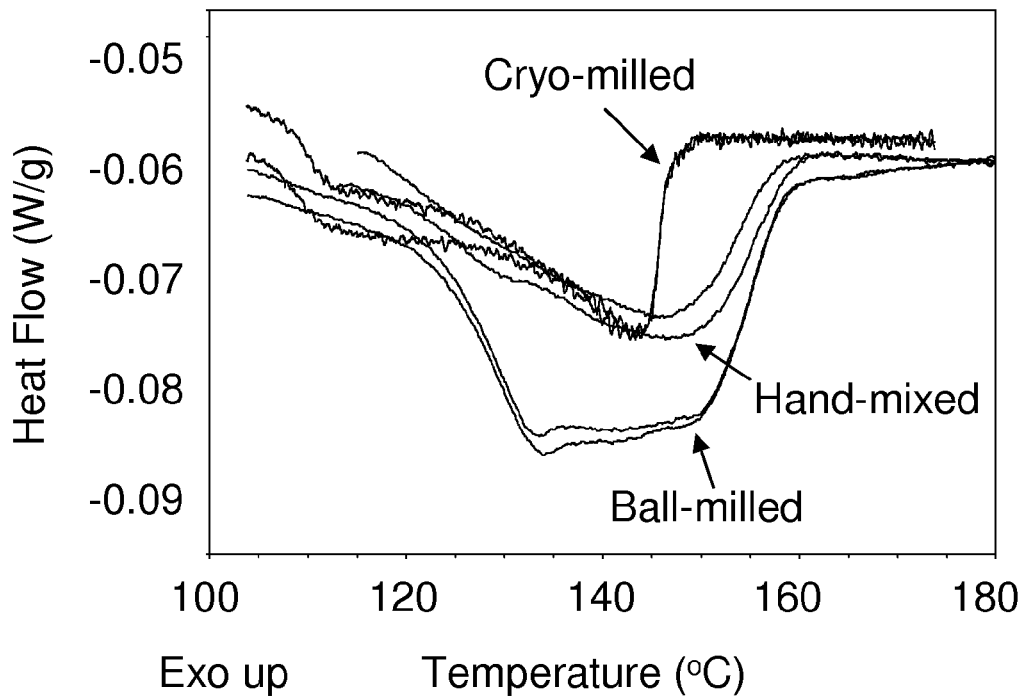
FIG. 1 shows the dissolution endotherms of 30 w/w % D-mannitol in PVP K15 prepared by cryomilling (16 minutes), hand mixing (10 minutes), and ball milling (30 minutes).

Three ways of mixing the components were tested: hand mixing, ball milling, and cryomilling. FIG. 1 shows that the cryomilled sample had smaller heat of dissolution and lower dissolution endpoint $T_{end}$ than the ball-milled and hand-mixed samples. This effect arises because cryomilling mixed the components more thoroughly than the other two methods and partially reduced the crystallinity of D-mannitol. As a result, the dissolution endpoint could be observed without substantial overheating.

Figure 2:
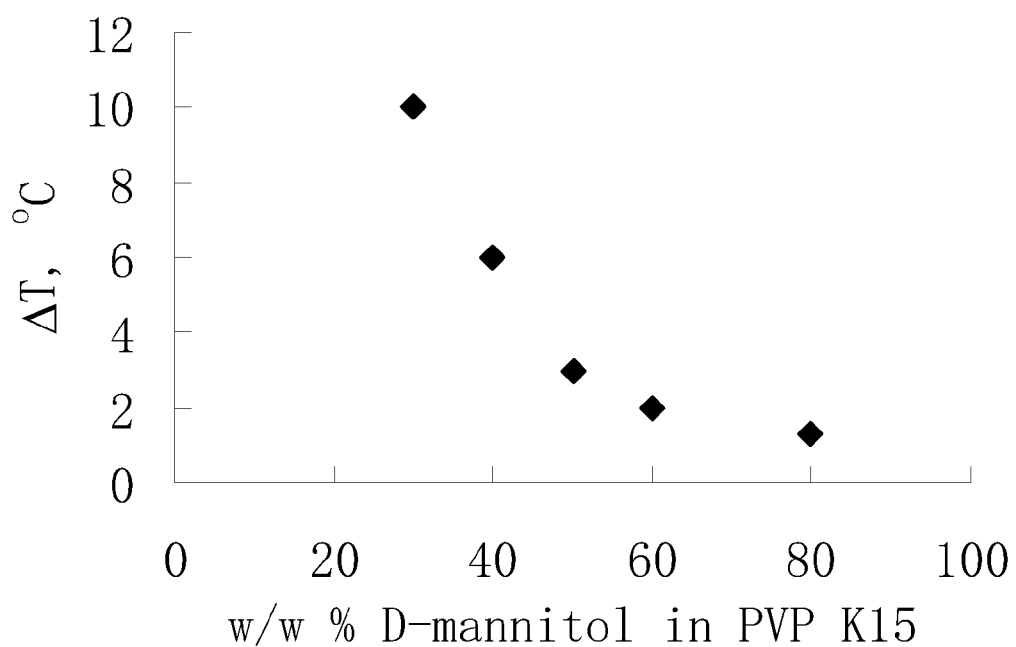
FIG. 2 shows the difference in end set temperature between hand-mixed and cryo-milled samples.

FIG. 2 shows how cryogenic milling facilitates the dissolution of D-mannitol in PVP K15. ΔT is the difference in $T_{end}$ between hand-mixed and cryo-milled samples. The hand-mixed samples were ground with mortar and pestle for up to 10 min. The cryo-milling time was between 16 to 20 min. The samples were heated at 0.5° C./min in DSC. The benefit of cryomilling is more pronounced for samples of lower solute concentrations. At high solute concentrations, ΔT was about 2° C. As the solute concentration decreased, ΔT increased up to 10° C. This difference is caused by the increase of the system's viscosity with the decrease of solute concentration (increase of polymer concentration). Overheating due to poor mixing is expected to be greater when the system's viscosity is higher and can be more effectively suppressed by cryomilling.

We used milling times from a few minutes to one hour, and determined that the optimal milling time was approximately 16 minutes for D-mannitol/PVP system. Adequate milling was found important at lower D-mannitol concentrations; for example, at 30% w/w D-mannitol, the reduction of $T_{end}$ by changing the milling time from 2 to 32 minutes was 10° C., with milling longer than 16 minutes offering little further lowering of $T_{end}$. The effects of cryomilling likely include mixing between the two components, reducing the particle size, and reducing crystallinity of the crystalline D-mannitol. The much lower $T_{end}$ from longer milling was attributed to the improved mixing because when the two components were individually cryomilled and then cryomilled together for 4 min, the $T_{end}$ was comparable to that of 4 min cryo-milling without the previous individual milling. The improved mixing between D-mannitol and PVP made sure that every crystal of D-mannitol was surrounded by PVP particles so that the components needed minimal time to diffuse and mix with PVP molecules upon heating.

Example 2

Figure 3:
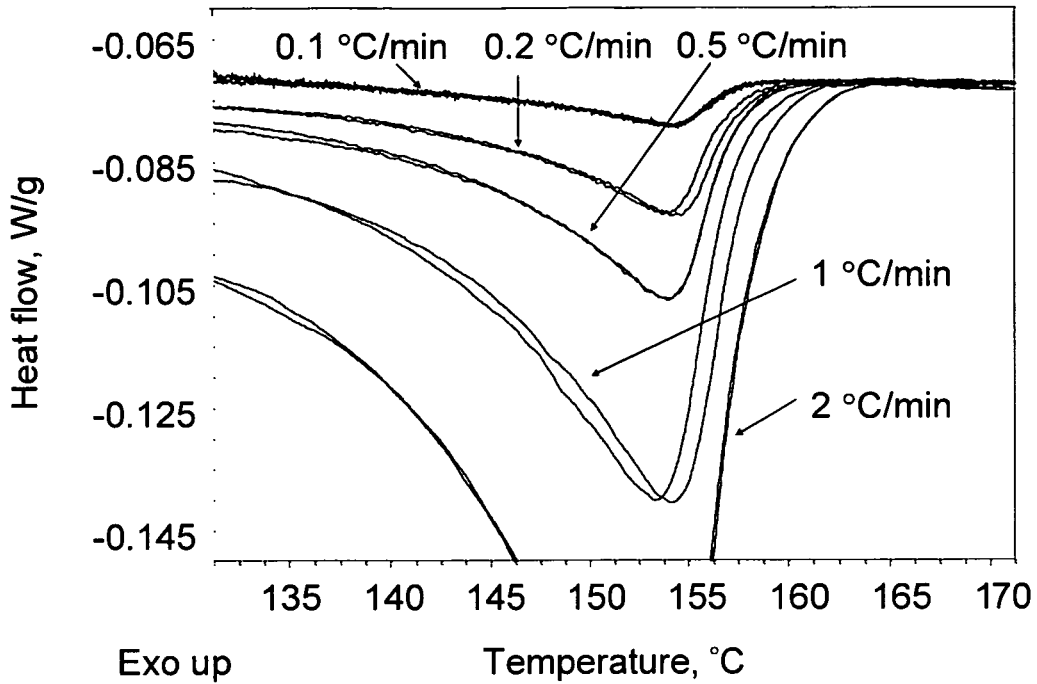
FIG. 3 shows dissolution endotherms measured at different heating rates for 60% w/w D-mannitol in PVP K15.
Figure 4:
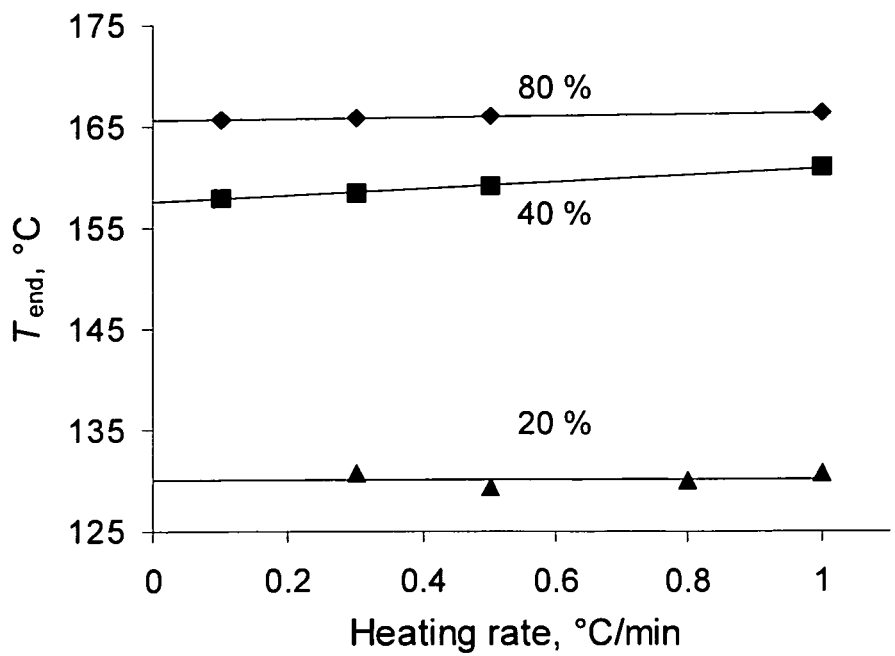
FIG. 4 shows $T_{end}$ extrapolation for D-mannitol in PVP K15 at different concentrations (80, 40, and 20% w/w).
Figure 5:
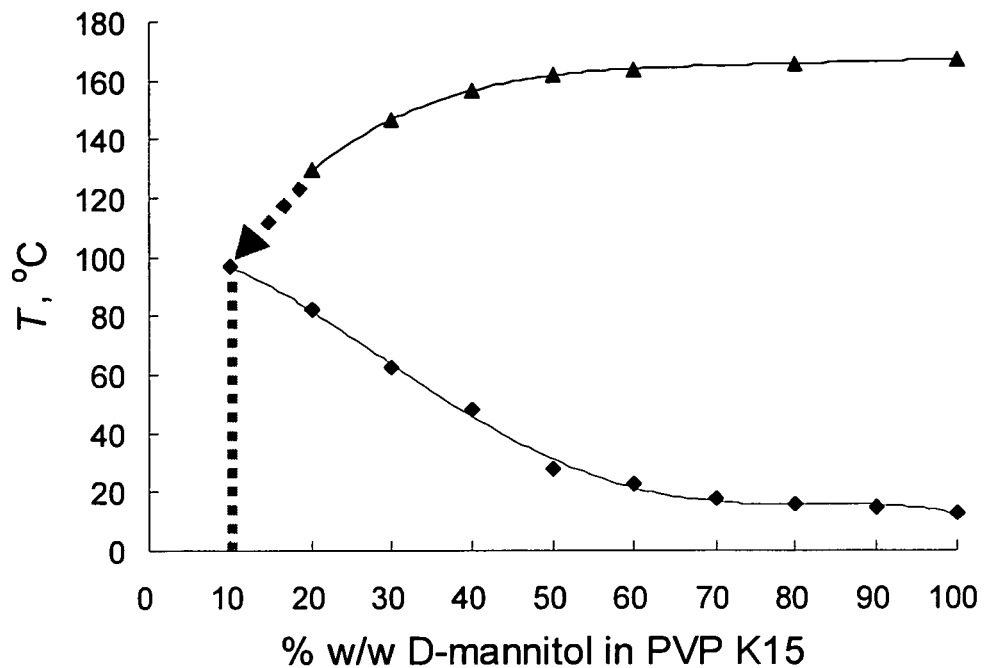
FIG. 5 shows the $T_{end}$ (triangle) and Tg (diamond) as a function of concentration. The dashed lines show the estimated solubility when the solution is at the glass transition temperature.

Solubility of D-Mannitol in PVP Near Tg Measured by the DSC Dissolution-Endpoint Method Having established the cryomilling was the preferred method for preparing mixtures, we applied the method to a series of D-mannitol/PVP mixtures to measure the solubility of D-mannitol in PVP. To further minimize the effect of slow dissolution on the measurement of equilibrium solubility, we measured $T_{end}$ at several heating rates (FIG. 3) and obtained the $T_{end}$ at zero heating rate by extrapolation (FIG. 4). It was observed that cryomilling substantially reduced the heating rate dependence of $T_{end}$, making the extrapolation more confident. The procedure could be confidently carried out down to approximately 20% w/w D-mannitol in PVP; at the still lower concentrations, the mixture was too viscous and the dissolution endotherm too weak for the method to work properly. The last point can be appreciated in reference to FIG. 5, which shows how much the dissolution endpoint $T_{end}$ is above the glass transition temperature of the mixture Tg. Tg is the temperature at which a liquid loses its ability to flow. Shown in FIG. 5 is the inflection point of the glass transition.

Because D-mannitol has low Tg (10° C.), its dissolution in PVP lowered the mixture's Tg and in turn, accelerated the dissolution process. As the concentration of D-mannitol decreased, the difference between the $T_{end}$ and Tg of the solution became smaller. The larger the difference ($T_{end}$-Tg), the lower the viscosity of the solution in which D-mannitol completed its dissolution. If the solution had low viscosity, dissolution was kinetically facile and $T_{end}$ did not depend strongly on the heating rate, as in the case for the mixtures shown in FIG. 3. As the concentration of D-mannitol decreased, however, $T_{end}$ approached Tg and dissolution eventually became too slow for the system to achieve solubility equilibrium even at the slowest heating rate practical. For such systems, $T_{end}$ changed rapidly and non-linearly with the heating rate, making the extrapolation to zero heating rate less certain. It was observed that at 10% w/w D-mannitol in PVP, the $T_{end}$ at 0.1° C./min heat rate was even higher than that observed at 20% w/w. This signified inability to reach solubility equilibrium owing to slow liquid dynamics and approximately defined the working limit of our method. Despite this limitation the method enabled us to get sufficiently close to Tg to estimate the solubility of D-mannitol in PVP at Tg: by extrapolation. In this way we found that the solubility of D-mannitol in PVP is 15% w/w at 105° C. and 10% w/w at 95° C. At 95° C., the saturated solution exists at the glass transition temperature.

Figure 6:
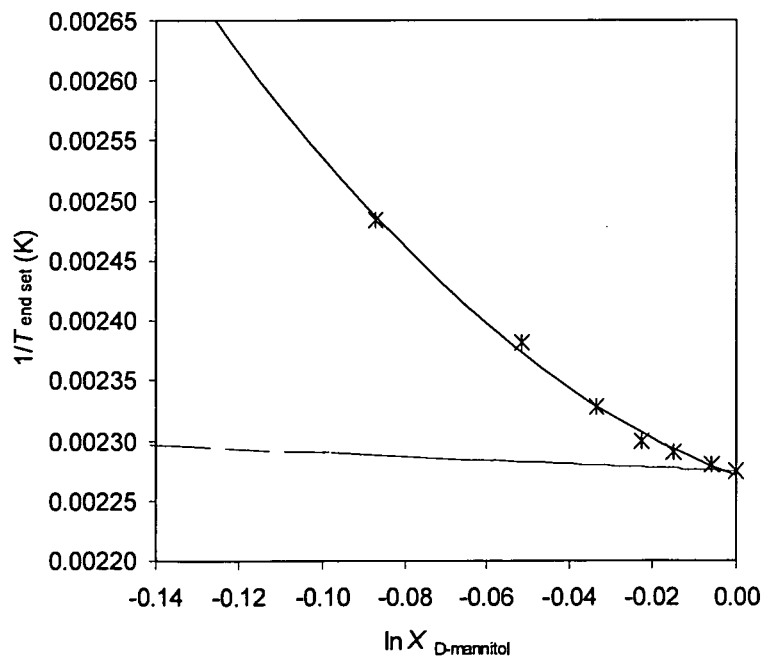
FIG. 6 shows a comparison of observed and ideal solubility of D-mannitol in PVP. The dashed line shows ideal solubility.

FIG. 6 shows the measured solubility temperature relation in the ln x–1/T format. In this format, the data are readily compared with the theory of ideal solubility, which predicts $$\ln X_{D-mann} = \frac{\Delta H}{R}\left(\frac{1}{T_f} - \frac{1}{T}\right)$$

where X is the mole fraction of D-mannitol, ΔH the heat of fusion, and $T_f$ the m.p. of pure D-mannitol, and T is the temperature at which X is to be evaluated. The observed solubility is substantially higher than predicted, indicating the D-mannitol PVP solution is not ideal.

Example 3

Validation of the DSC Dissolution-Endpoint Method for the D-Mannitol/PVP System

Figure 7:
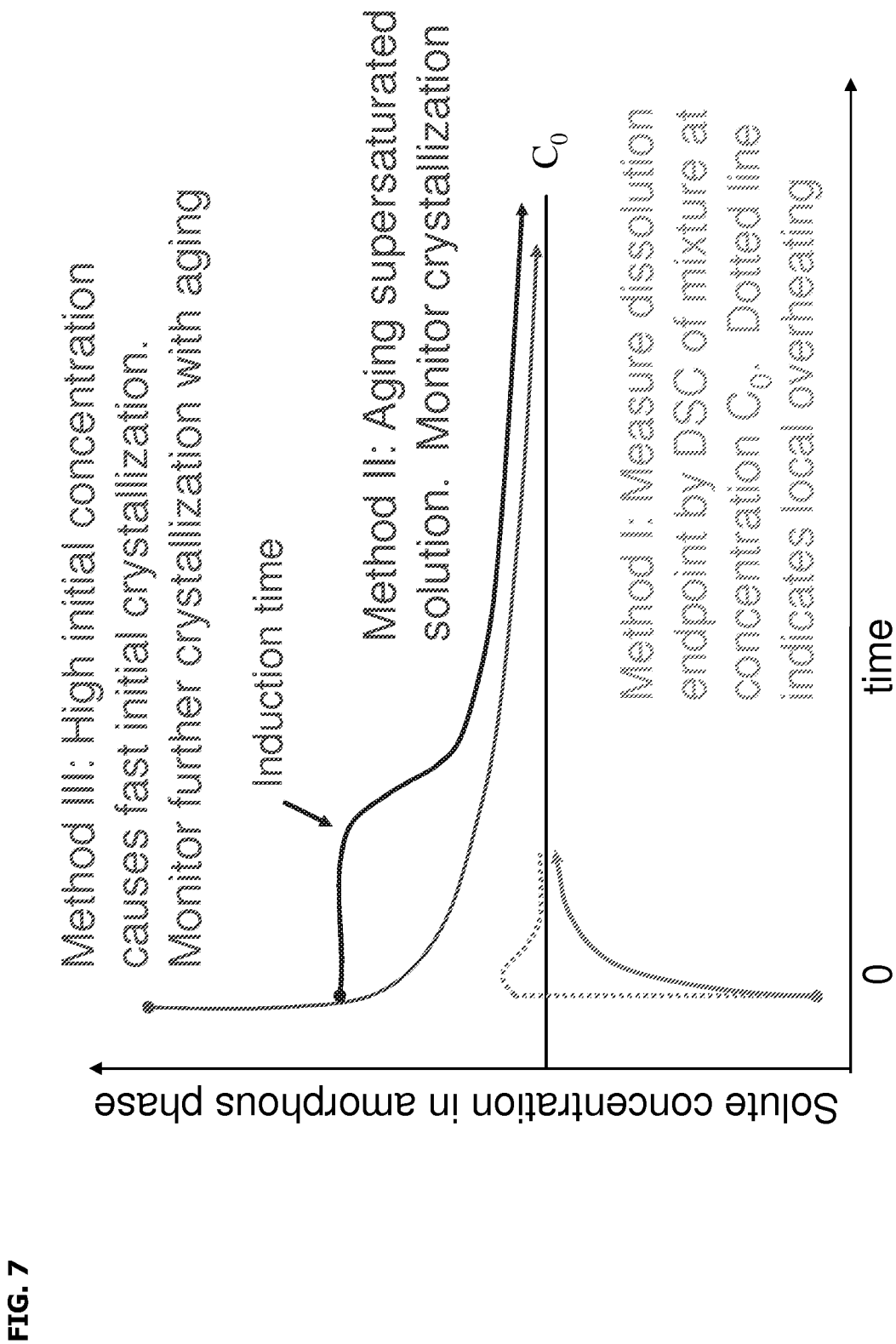
FIG. 7 shows three different approaches to obtain the solubility of D-mannitol in PVP.

To verify the solubility of D-mannitol in PVP obtained with the DSC method (Method I), we used two other solubility-indicating methods (FIG. 7). In the first (Method II), D-mannitol was mixed with PVP at a concentration higher than predicted. The mixture was then aged to see whether the supersaturated solution indeed crystallized over time. We tracked three indicators of crystallization: (a) the glass transition temperature Tg of the mixture, which is expected to increase when D-mannitol is removed from its mixture with PVP (FIG. 5); (b) the appearance of new endotherms with aging which correspond to the dissolution of newly crystallized D-mannitol; and (c) new crystals observable by polarized light microscopy. Modulated DSC (MDSC) was used to measure Tg. In the second method (Method III), D-mannitol was mixed with PVP at high enough concentration so that D-mannitol rapidly crystallized. The remaining amorphous phase was now seeded to promote further crystallization during aging. Because Method III introduced crystal seeds at time zero, we expected that the time required to reach solubility equilibrium with Method III would be shorter than that with Method II, which required nucleation.

We chose 105° C. as the temperature for these tests, at which the predicted solubility is 15%. For Method II, D-mannitol was mixed with PVP by cryogenic milling at 30% w/w. The mixture was melted in several DSC pans on a microscope hot stage and the resulting solution was aged at 105° C. The mixture was analyzed by DSC at times ranging from a few days to 155 days. We found that the Tg of the mixture increased upon aging (FIG. 8a). Simultaneously, a melting endotherm of D-mannitol appeared at approximately 155° C., which resulted from the melting of D-mannitol crystals formed during aging at 105° C. The D-mannitol crystals formed at 105° C. belonged to the δ polymorph; this was confirmed by the melting point and X-ray diffraction. In 155 days, the Tg of the mixture increased from 70 to 95° C. and the step size of the glass transition became smaller, indicating that the amount the amorphous phase had become smaller. Meanwhile, the melting endotherm of D-mannitol increased. Visual observations with the aid of polarized light microscopy verified that the 30% D-mannitol in PVP was initially amorphous but on aging at 105° C. yielded crystals of D-mannitol. These results confirm that the 30% solution of D-mannitol in PVP is supersaturated at 105° C. Moreover, the results suggest that the saturated solution at 105° C. contains approximately 12% of D-mannitol, which roughly matches the solubility estimated with Method I.

To carry out Method III, 60% D-mannitol was first dissolved in PVP by melting. The liquid was cooled to 110° C. and allowed to crystallize. Visual observations showed that crystals of D-mannitol's δ polymorph formed throughout the material. This fast crystallization, though occurring everywhere, could not completely crystallize all the D-mannitol above the saturation limit and the remaining amorphous phase still contained excess D-mannitol. Different from the amorphous phase in Method II, this amorphous phase was in contact with D-mannitol crystals formed in situ. Upon aging at 105° C., D-mannitol crystallized further, with crystalline D-mannitol serving as seeds to the amorphous phase. The Tg of the samples was determined by MDSC at different aging times. We observed that after 2 days of aging at 105 C, Tg increased by about 10° C. With longer aging, the Tg continued to increase up to approximately 50 days. Due to the lower polymer concentration in this experiment relative to that in Method II, the glass transition was weaker and more difficult to measure. Overall, the results of Methods II and III support the conclusion reached with Method I.

Example 4

Solubility of IMC and Nif in PVPVA Near the Glass Transition Temperatures

After validating the DSC dissolution-endpoint method (Method I), we applied it to measure the solubility of nifedipine (NIF) and indomethacin (IMC) in a copolymer of 60 wt. % N-vinylpyrrolidone and 40 wt. % vinyl acetate (PVPVA64). Both drugs are poorly water-soluble and have similar molecular weight, Tg (42° C.), and Tm. NIF crystallizes faster than IMC. As in the case of D-mannitol/PVP, cryomilling was used to prepare drug/polymer mixtures. The cryomilling time was up to 14 min for IMC/PVPVA64 and up to 20 min for NIF/PVPVA64. Unlike the D-mannitol/PVP system, the maximal milling time for these two systems was determined by how long the drug could be milled without completely losing crystallinity (cryomilling IMC alone is known to completely destroy its crystallinity). As in the case of the D-mannitol/PVP, cryomilling facilitated the determination of dissolution endpoint. As FIG. 10 illustrates, longer cryomilling led to lower dissolution endpoint, as did its dependence on heating rate. Again, this effect was more pronounced at low drug concentrations.

FIG. 11 shows how the dissolution endpoint $T_{end}$ and the glass transition temperature Tg (onset) changed with drug concentration for the two systems. The lowest drug concentration for which these measurements were made was 40% w/w IMC in PVPVA64, whose $T_{end}$ was 33° C. above its Tg, and 25% w/w NIF in PVPVA64, whose $T_{end}$ is 34° C. above its Tg. As explained earlier, the closer a liquid approaches its Tg, the higher its viscosity, and the more difficult it is to achieve solubility equilibrium during DSC scan. Our solubility measurements have approached the Tg sufficiently to enable us to estimate the solubilities of IMC and NIF in PVPVA by extrapolation. The extrapolation is shown in FIG. 10 as dotted lines. We found that the solubility of IMC in PVPVA is approximately 28% w/w at 85° C. and this saturated solution exists at the glass transition. We found that the solubility of NIF in PVPVA is approximately 12% w/w at 95° C. and this saturated solution exists at the glass transition temperature. As in the case of D-mannitol/PVP (FIG. 6), the observed solubilities of IMC in PVPVA and NIF in PVPVA greatly exceed those predicted by the theory of ideal solubility.

FIG. 12 compares the solubilities determined for the three systems: D-mannitol/PVP, IMC/PVPVA, and NIF/PVPVA. At the same temperature, the molar solubility of IMC in PVPVA is higher than NIF in PVPVA and the molar solubility of D-mannitol in PVP is lower than those of IMC and NIF in PVPVA. This rank order of solubility agrees with the theory of ideal solubility. Because D-mannitol, IMC, and NIF have similar melting points, the theory predicts that their solubilities are ordered by their heats of fusion, with the solute of higher heat of fusion having lower solubility. The heats of fusion for the three solutes are 52.1 kJ/mol (β D-mannitol) (Burger, A.; Henck, J.-O.; Hetz, S.; Rollinger, J. M.; Weissnicht, A. A.; Stöttner, H. J. Pharm. Sci. 2000, 89, 457), 39.3 kJ/mol (α NIF) (Zhou, D.; Grant, D. J. W.; Zhang, G. G. Z.; Law, D.; Schmitt, E. A. J. Pharm. Sci. 2006, 96(1), 71-83), and 37.4 kJ/mol (γ IMC) (Wu, T.; Yu, L. J. Phys. Chem. B 2006, 110, 15694-15699). The solubility of NIF in PVPVA64 was slightly lower than IMC.

Example 5

Validation of the DSC Dissolution-Endpoint Method: Solubility of NIF in NMP

The solubility of NIF in 1-methyl-2-pyrrolidone (NMP), the monomer of PVP, is reported to be 17.4% w/w at 25° C. (Marsac, P. J.; Shamblin, S. L.; Taylor, L. S. Pharm. Res. 2006, 23(10), 2417-2426). FIG. 13 plotted the data of NIF/NMP solubility measured at higher temperatures by DSC dissolution-endpoint method and the reported solubility at 25° C. The linearity of the combined data set throughout the temperature range demonstrates the agreement of the DSC method and the conventional shake-flask solubility method.

Example 6 (Prophetical)

Increasing the Upper Concentration Limit of a Solid Solution

As shown in FIG. 14, several theoretical approaches could be taken to increase the UCL. They are illustrated briefly below taking "a" as the UCL of the reference formulation.

Approach 1: increasing $T_g$ of the polymeric matrice while maintaining the interaction between the drug and the matrice (Thus maintaining the $T_{end}$—composition curve). The UCL increases from a to b.

Approach 2: Maintaining the $T_g$—composition curve while increasing the interaction between the drug and the matrice (Thus lowing the $T_{end}$—composition curve). The UCL increases from a to c.

Approach 3: increasing $T_g$ of the polymeric matrice while increasing the interaction between the drug and the matrice (Thus lowing the $T_{end}$—composition curve) simultaneously. The UCL increases from a to d.

In reality, $T_g$ and $T_{end}$ may not be manipulated independently. Most likely, changing one of the formulation components impacts on both on $T_g$ and $T_{end}$. In these cases, careful experiments and analyses need to be performed to evaluate, more quantitatively, the benefit of such modifications on physical stability of the formulations.

We claim:

1. A method for evaluating the solubility of a crystalline substance in a polymer, comprising
    a) providing an intimate non-amorphous mixture of the crystalline substance and the polymer,
    b) heating the intimate non-amorphous mixture while recording the DSC dissolution endotherm of the mixture,
    c) determining an endset temperature of dissolution $T_{end}$ from the DSC dissolution endotherm,
    d) taking $T_{end}$ as the temperature at which the crystalline substance dissolves completely in the polymer.

2. The method of claim 1, wherein the intimate non-amorphous mixture is obtained by joint cryo-milling of the crystalline substance and the polymer.

3. The method of claim 1, comprising recording the DSC dissolution endotherm at a plurality of heating rates and extrapolating $T_{end}$ to zero heating rate.

4. A method for evaluating the solubility of a crystalline substance in a polymer as a function of temperature, comprising
    a) providing a plurality of intimate non-amorphous mixtures of crystalline substance and polymer having different compositions,
    b) determining $T_{end}$ of each of the intimate non-amorphous mixtures by the method of claim 1,
    c) plotting $T_{end}$ over the composition of the mixtures.

5. A method for evaluating the solubility of a crystalline substance in a polymer at the glass transition temperature Tg, comprising
    a) establishing the solubility of the crystalline substance in the polymer as a function of temperature by the method of claim 4,
    b) providing a plurality of crystalline substance and polymer non-amorphous mixtures having different compositions and determining Tg of a liquid formed by melting each of the non-amorphous mixtures,
    c) plotting Tg over the composition of the non-amorphous mixtures, d) determining the solubility at Tg as the intersection of the $T_{end}$ plot and the Tg plot.

6. The method of claim 5, wherein Tg is determined by a DSC method.

7. The method of claim 5, wherein the crystalline substance is a pharmaceutically active ingredient.

8. The method of claim 1, wherein the intimate non-amorphous mixture of the crystalline substance and the polymer is a powder mixture.

* * * * *